United States Patent
Teufel

(10) Patent No.: US 6,261,604 B1
(45) Date of Patent: Jul. 17, 2001

(54) SOIL AMENDMENT WITH INSECT CONTROL CAPABILITIES

(76) Inventor: George R. Teufel, 13131 NW. Laidlaw Rd., Portland, OR (US) 97229

( * ) Notice: Subject to any disclaimer, the term of this patent is extended or adjusted under 35 U.S.C. 154(b) by 0 days.

(21) Appl. No.: 08/163,902

(22) Filed: Dec. 6, 1993

(51) Int. Cl.[7] .................................................. A01N 59/00
(52) U.S. Cl. ............................................................ 424/724
(58) Field of Search ................................. 71/11, 23, 25, 71/62, 901; 424/405, 406, 724

(56) References Cited

U.S. PATENT DOCUMENTS

| | | | |
|---|---|---|---|
| 4,494,975 | * | 1/1985 | De Boodt et al. ........................ 71/25 |
| 5,114,894 | | 5/1992 | Witt ........................................ 502/62 |
| 5,145,492 | * | 9/1992 | Weiergräber ............................ 55/17 |

OTHER PUBLICATIONS

Arthur Dammann: A Preliminary Study of the Uses of Pacific Northwest Diatomite (1939) (pp. 51–60).
Robert Calvert: Diatomaceous Earth (1930) (pp. 89–90 and 104–105).
Floyd Allen: A Natural Earth That Controls Insects (1972) (pp. 50–56).
Robert Calvert: Diatomaceous Earth (1930) (pp 89–90 and 104–105) , Chemical Catalog Company, NY.*
Floyd Allen: A Natural Earth That Controls Insects (1972) Organic Gardening and Farming, p 50–56.*

* cited by examiner

*Primary Examiner*—S. Mark Clardy
(74) *Attorney, Agent, or Firm*—Miller Nash LLP

(57) ABSTRACT

The invention disclosed here is a method for making an insecticidal soil amendment from brewery diatomite. The invention involves mixing diatomaceous earth or "diatomite" which had a prior use as a filtering agent in a brewery with raw, finely ground, tree bark. The mixture is composted together for a certain period of time. The composting process removes organic particulates from the brewery diatomite, which were present as a result of its use as a filtering agent, and regenerates the insecticidal properties of the fossilized diatoms making up the diatomite. At the same time, the decaying organics provide composting nutrients for the tree bark making it better suited for use as a soil amendment.

4 Claims, No Drawings

SOIL AMENDMENT WITH INSECT CONTROL CAPABILITIES

TECHNICAL FIELD

This invention generally relates to the use of diatomaceous earth as an insecticidal agent. More particularly, it relates to the use of diatomaceous earth as a non-toxic soil additive for controlling insects in plant beds.

BACKGROUND INFORMATION

Diatomaceous earth consists of the skeletal or fossilized remains of diatoms, which are microscopic, flowerless water plants related to algae. Diatoms were an early form of life on earth and remain abundant today. They are too small to be seen individually without magnification. Collectively, they will often appear as a brown growth on the surface of stagnant water, mud, rocks, seaweed, or wherever light and water have coexisted for a sufficiently long time for diatoms to propagate and accumulate. Diatoms live in both fresh and salt water.

Over a long period of time, decaying diatoms accumulate on lake and sea beds. In many areas of the world, ancient lake or sea beds, which are now on dry land, contain massive layers of fossilized diatoms. These layers are mined as diatomaceous earth.

Diatomaceous earth is nearly pure silica and has a chalky or flour-like feel when rubbed between one's fingers. A microscopic examination of the fossilized diatoms making up diatomaceous earth would reveal that they are small particles having numerous sharp edges and splines.

Since fossilized diatoms originally consisted of vegetable matter, diatomaceous earth is non-toxic to humans and animals if ingested, and is otherwise harmless because of the small size of diatoms. For this reason, diatomaceous earth is sometimes called "fossil flour" because of its use as animal feed, and its reported use as a flour supplement in baking bread in certain impoverished countries.

Diatomaceous earth has enjoyed many other kinds of uses as well. For example, it has been used as an additive for concrete, as an insulating material, and has enjoyed widespread use as a filtering agent. As will become apparent, the present invention relates to the latter use.

Approximately 40 years ago, it was discovered that diatomaceous earth could serve as an effective insecticidal agent. Unlike human beings and other animals, insects have exoskeletons. Basically, an insect exoskeleton is a hard but porous cover which contains and protects vital internal fluids. The exterior surface of the exoskeleton is covered and protected by an oily or waxy layer which seals it and prevents the escape of moisture and internal fluids.

If an object is small and sharp enough, it will scratch the covering layer, thereby allowing the internal fluids to escape from inside the exoskeleton. The resultant effect is that the insect will dehydrate and die. Consequently, the sharp, microscopic edges of the diatom particles making up diatomaceous earth can be fatal to insects upon contact. The obvious advantage that diatomaceous earth offers over chemical insecticidal agents is that diatomaceous earth is entirely mechanical and non-toxic in the way it kills insects.

Breweries use milled diatomaceous earth as a filtering agent in connection with making beer. When used for such purpose, the diatomaceous earth must be replaced periodically because it eventually becomes clogged with filtered organic matter. It is not reusable and has created a disposal problem for the brewing industry.

It is believed that, in most cases, breweries ship their unusable diatomaceous earth to landfills for burial. This is costly from the standpoint of shipping and handling. Because of its non-toxic nature, and since the filtered organics contain sugars, yeasts, and proteins which have nutritional value, in some cases the used diatomaceous earth has been fed to animals. In this respect, and for the same reason that diatomaceous earth is fatal to insects, it is believed that such use helps to control certain internal parasites in animals. However, it is not believed that the demand for use as animal feed is sufficient to utilize more than a small percentage of total brewery waste output.

The present invention addresses the above brewery disposal problems. For the reasons stated above, it is admittedly well-known in the prior art for nurseries and others to use freshly mined and milled diatomaceous earth as a soil additive or amendment for the purpose of insect control. However, diatomaceous earth is not suitable for such use after it has been used as a filtering agent in a brewery.

If the used filtering agent is added to or mixed with soil, the retained organics which were filtered would cause molds and fungal diseases to develop in the soil. The retained organics would also create a physical change in the soil that would inhibit proper soil porosity. With respect to insect control, the retained organics fill the spaces in between the edges of the fossilized diatoms making up the filtering agent, blunting their effectiveness with respect to their ability to scratch the outer covering of an insect exoskeleton. Last, the filtered organics also have a very rancid smell which makes it undesirable to use them as part of a soil additive near residences.

For the reasons stated above, diatomaceous earth having a prior use as a filtering agent in a brewery is not suitable nor effective for use as an insecticidal soil amendment. The purpose of the present invention, therefore, is to convert the used filtering agent into a form that will be suitable for such use. The practical advantage the invention provides to nurseries is that an excellent product is created from the standpoint of producing a soil amendment that adds to soil quality and fertility, while, at the same time, provides a degree of non-toxic insect control. The commercial advantage is that filtered diatomaceous earth can be obtained from breweries at little cost in comparison to obtaining freshly mined diatomaceous earth. How the invention accomplishes the above advantages and objectives is disclosed below.

SUMMARY OF THE INVENTION

The invention is a method of making an insecticidal soil amendment by mixing a used filtering agent from a brewery process with a compostable material. The filtering agent consists of diatomaceous earth and retained filtered organic particulates resulting from the brewery process. Diatomaceous earth is also called "diatomite," which is the term that is often used here. Diatomite having a prior use as a filtering agent in a brewery process will sometimes be referred to as "brewery diatomite."

In accordance with the invention, the mixture of brewery diatomite and the compostable material is allowed to compost a sufficient amount of time to cause decay of both the compostable material and the organic particulates retained in the brewery diatomite. During the composting process, the retained organic particulates decay and provide nutrients to the compostable material, thereby assisting its decay. At the same time, the decay of the particulates also "regenerates" the microscopic edges of the fossilized diatoms making up the brewery diatomite, making them once again effective in controlling insects.

Ground tree bark may be used as the compostable material mentioned above. This material normally does not compost well without the introduction of proper amounts of organic nutrients, water, and air. Composting the brewery diatomite with ground tree bark therefore has the advantage of making the bark better suited as a soil amendment than it would otherwise be.

Moreover, regardless of the degree to which tree bark is ground, it will normally have small-sized splinters which can stick into human skin. During the mixing and composting process described above, the regenerated sharp edges of the diatoms cause them to be attached to the exterior surfaces of individual bark dust particles and splinters. This provides an additional advantage in that the resultant diatomite "coating" substantially reduces harm from splinters.

The invention as summarized above will become better understood upon review of the following description.

BEST MODE FOR CARRYING OUT THE INVENTION

The present invention is not amenable to illustration, given that it is essentially a chemical process in nature.

When used as a filtering agent, diatomite is initially very porous to the transmission of liquid. Generally, the diatomite has been finely ground, breaking up the shells of individual fossilized diatoms and exposing their sharp edges. The air spaces between the edges permit the transmission of fluids for filtration purposes.

After a period of use as a filtering agent in a brewery process, the air spaces between the diatom edges gradually become clogged with organic particulates. Eventually, these particulates build up to the extent such that they impede further fluid transmission. At that point, the used diatomite must be replaced.

As was explained earlier, used brewery diatomite cannot be directly added to soil as an insecticidal soil amendment. Therefore, and in accordance with what is considered to be the invention here, the brewery diatomite is taken and mixed with finely ground tree bark. The mixture of brewery diatomite and tree bark is then allowed to compost in the conventional way.

The composting process itself would be well understood by the skilled person. In some cases, it may be necessary to add water and other nutrients to assist the composting process. For the most part, however, the combination of raw tree bark and brewery diatomite is mutually beneficial in the composting process. The tree bark benefits from the available proteins, sugars, yeasts, and moisture present in the brewery diatomite, all of which assist composting. The brewery diatomite benefits in that the organic particulates which it carries are removed, thereby regenerating the clogged diatom edges for use as an insecticidal agent. Essentially, this is accomplished by the heat and chemical action of the composting process which dries and aerates the fossilized diatoms.

The finished product, after composting, is a very attractive soil amendment. It has the ability to control certain insects that come into contact with the soil because the microscopic edges of the diatomite are once again exposed. However, it remains non-toxic to mammals because the edges cannot penetrate fur or skin. Also, the regenerated and exposed edges cause diatom particles to attach directly to bark dust particles. This inhibits the ability of splinters to enter skin when hand work is done in flower or nursery beds where the soil amendment is present.

The invention as described above provides a unique way of disposing of one particular kind of waste product, i.e., brewery diatomite that has been used as a filtering agent. It is not presently believed that the invention has similar application for the disposal of other kinds of diatomite waste products, with the exception that it is conceivable that it could be used in connection with industries other than breweries where diatomite is used to filter certain kinds of organic matter.

Used brewery diatomite is unique from the standpoint of its use as a filtering material, the chemical nature of the filtered organics, plus the ability of diatomite to control insects. Although raw tree bark or bark dust was described above as being the preferred material for use in mixing and composting brewery diatomite, it is conceivable that other kinds of compostable materials could be used in replacement of bark dust.

Because certain unanticipated changes could be made to the invention as described above without departing from what is considered to be the invention, it is to be understood that the invention is not to be limited by the foregoing description. Instead, the invention is to be defined and limited exclusively by the individual claim or claims which follow, the interpretation of which is to be made in accordance with the established doctrines of patent claim interpretation.

What is claimed is:

1. A method for making an insecticidal soil amendment, comprising:

mixing a used filtering agent and a compostable material, the filtering agent being characterized in that the filtering agent includes diatomite that has retained certain organic particulates resulting from a prior use of the filtering agent, and composting the mixture a sufficient amount of time to cause decay of both the compostable material and the organic particulates retained by the diatomite, the composted mixture together forming the insecticidal soil amendment, and further, the decayed organic particulates providing nutrients for the resultant soil amendment.

2. The method of claim 1, wherein the filtering agent is a by-product of a brewery process.

3. A method for making an insecticidal soil amendment, comprising:

mixing a used filtering agent and ground tree bark, the filtering agent being substantially composed of diatomite that has retained certain organic particulates resulting from prior use of the filtering agent in a brewery process, the organic particulates not normally being desirable for use as a soil additive and also interfering with the ability of the diatomite to act as an insecticidal agent, and composting the mixture of the used filtering agent and ground tree bark a sufficient amount of time to cause decay of the organic particulates retained by the diatomite, such decay creating organic nutrients for composting the mixture and making the diatomite usable as an insecticidal agent, the composted filtering agent and tree bark together forming the insecticidal soil amendment.

4. The method of claim 2, wherein the filtering agent is a by-product of a brewery process.

* * * * *